United States Patent [19]

Franke, deceased et al.

[11] Patent Number: 4,945,114

[45] Date of Patent: Jul. 31, 1990

[54] THERAPEUTIC AGENTS CONTAINING ENANTIOMERS OF PROPAFENONE

[75] Inventors: Albrecht Franke, deceased, late of Wachenheim, by Renate E. Franke, Catharina Franke, legal representatives; Rainer Schlecker, Bissersheim; Josef Gries, Wachenheim; Gerda Von Philipsborn, Weinheim; Liliane Unger, Ludwigshafen, all of Fed. Rep. of Germany

[73] Assignee: BASF Aktiengesellschaft, Ludwigshafen, Fed. Rep. of Germany

[21] Appl. No.: 225,756

[22] Filed: Jul. 29, 1988

[30] Foreign Application Priority Data

Jul. 30, 1987 [DE] Fed. Rep. of Germany ....... 3725273

[51] Int. Cl.$^5$ .......................................... A61K 31/135
[52] U.S. Cl. .................................. 514/652; 514/821
[58] Field of Search ................................ 514/652, 821

[56] References Cited

U.S. PATENT DOCUMENTS 4,460,605  7/1984  Petrik et al. ........................ 514/652
4,571,409  2/1986  Frank et al. ........................ 514/652

OTHER PUBLICATIONS

Liebigs Ann. Chem., 1987, pp. 561–563, Blaschke, et al., Racemattrennung von Propafenon und Diprafenon, Konfiguration . . .

*Primary Examiner*—Frederick E. Waddell
*Attorney, Agent, or Firm*—Oblon, Spivak, McClelland, Maier & Neustadt

[57] ABSTRACT

Therapeutic agents containing enantiomers of propafenone, the preparation of the said agents and their use for certain groups of patients.

7 Claims, No Drawings

THERAPEUTIC AGENTS CONTAINING ENANTIOMERS OF PROPAFENONE

The present invention relates to drugs prepared from the propafenone enantiomers.

Propafenone (INN for 2'-(2-hydroxy-3-propylaminopropoxy)-3-phenylpropiophenone), with the structural formula

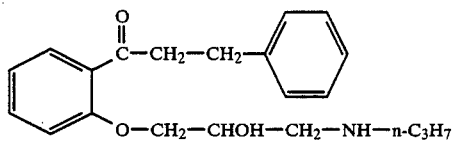

is successfully used in the form of the hydrochloride for the therapy of cardiovascular disorders, in particular of cardiac arrhythmias.

In addition to the antiarrhythmic action, propafenone has an additional β-sympatholytic action.

Propafenone has a center of asymmetry at carbon atom 2 of the aminopropanol side chain and has been used to date only in the form of the racemate. Although the racemate has already been resolved (G. Blaschke and B. Walther, Liebigs Ann. Chem. 1987, 561–563), the pharmacological properties of the enantiomers have not been investigated.

This investigation has now been carried out and surprising results were obtained, with considerable practical consequences, as will be described below.

The propafenone enantiomers can be obtained by stereospecific synthesis. In this procedure, the known phenol I is reacted with an optically active $C_3$ building block to give an intermediate (IV).

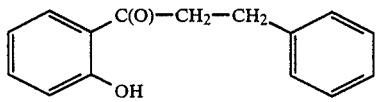

Examples of suitable $C_3$ building blocks are glycidol II or one of its derivatives III. In the formula III

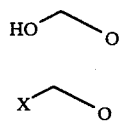

X is a nucleofugic leaving group (which can be displaced by nucleophiles), such as $CF_3SO_3$, $CH_3SO_3$, $CH_3-C_6H_4-SO_3$ or Br. Glycidol is obtainable in both enantiomeric forms (JOC 51 (1986), 3710), and the derivatives III can be prepared therefrom by known processes (JOC 43 (1978), 4876). These $C_3$ building blocks can also be prepared from natural substances, such as mannitol (Eur. J. Med. Chem. 17 (1982), 69 and TH 42 (1986), 447).

The reaction of I with II or III is carried out by processes known from the literature (Heterocycles 20 (1983), 1975; Eur. J. Med. Chem. 17 (1982), 69; JOC 51 (1986), 3710 and European Patent No. 6,615). Thus, glycidol can be etherified under the conditions of the Mitsunobu method, and the compounds III are reacted under the conditions of the Williamson synthesis. The reaction gives the optically active epoxide

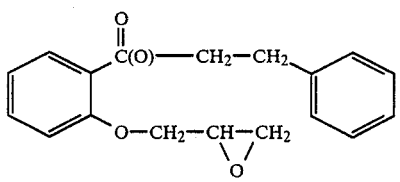

which is converted into (R)- or (S)-propafenone in a conventional manner.

As expected, the β-blocking action of (R,S)-propafenone is attributable to the (S)-enantiomer.

Table 1 shows that $^3H$-dihydroalprenolol binding (heart, lung) is inhibited to a significantly greater extent by the (S)-enantiomer and to a significantly smaller extent by the (R)-enantiomer compared with (R,S)-propafenone.

On the other hand, the enantiomers surprisingly do not differ from one another with respect to the antiarrhythmic action (Table 2). This finding was unexpected because the therapeutic effect of a racemate is usually due more or less substantially to one enantiomer. For example, the parent compound of the class I antiarrhythmics, quinidine, is effective only in the form of the 8(R),9(S)-enantiomer.

Thus, the propafenone enantiomers comprise two compounds which, because of their different action profile, are suitable for the selective therapy of cardiac arrhythmias of different groups of patients.

(S)-propafenone, with a more powerful β-blocking action than propafenone, is indicated for the following: for tachycardiac arrhythmias accompanied by high catecholamine levels and for patients who have not yet been treated with β-blockers.

The (R)-enantiomer, with a weaker β-blocking action than propafenone, is indicated for the following: for patients who are already under β-blocker therapy and for older patients (over about 50) and/or patients suffering from hypotension and/or cardiac insufficiency, in each of which cases β-blockers are contraindicated.

The present invention accordingly relates to therapeutic agents for systemic use which contain a propafenone enantiomer as the active compound, in addition to conventional pharmaceutical auxiliaries, and the preparation of a drug using a propafenone enantiomer.

The therapeutic agents or formulations are prepared using the conventional liquid or solid carriers or diluents and the conventional pharmaceutical auxiliaries, in accordance with the desired route of administration and in a dose suitable for use, preparation being effected in a conventional manner, for example by mixing the active compound with the solid and liquid carriers and auxiliaries conventionally used in such preparations.

The agents can be administered perorally or parenterally. Examples of formulations of this type are tablets, film tablets, coated tablets, capsules, pills, powders, solutions and suspensions as well as infusion or injection solutions.

Examples of conventionally used pharmaceutical auxiliaries are mannitol, lactose, propylene glycol and ethanol, gelatine, starch, talc, stearic acid and polyvinylpyrrolidone. Flavor improvers, stabilizers, emulsifiers, etc. can, if required, be added to the preparations. It is essential that all substances used in the preparation of the pharmaceutical formulations are toxicologically acceptable and compatible with the active compounds used.

If necessary, the novel enantiomers obtained are converted into an addition salt with a physiologically tolerated acid. A list of conventional physiologically tolerated acids is given in Fortschritte der Arzneimittelforschung 1966, Birkhäuser-Verlag, Vol. 10, pages 224-285, Germany, Switzerland. Hydrochloric acid is preferred.

The addition salts with acids are, as a rule, obtained in a conventional manner by mixing the free base or a solution thereof with the appropriate acid or a solution thereof in an organic solvent, for example a lower alcohol, such as methanol, ethanol or propanol, or a lower ketone, such as acetone, methyl ethyl ketone or methyl isobutyl ketone, or an ether, such as diethyl ether, tetrahydrofuran or dioxane. To improve deposition of crystals, mixtures of the stated solvents may be used. Furthermore, pharmaceutically acceptable aqueous solutions of addition compounds of the propafenone enantiomers with acids can be prepared by dissolving the free bases in an aqueous acid solution.

The contents of active compound in the novel pharmaceutical preparations are in the conventional range for propafenone preparations, i.e. from 0.1 to 50, preferably from 0.2 to 20, in particular from 1 to 5, mg per kg of body weight for a single dose in the form of the hydrochloride; i.e. for a patient weighing 70 kg, the content of active compound is from 7 to 3,500, preferably from 14 to 1,400, in particular from 70 to 350, mg.

METHODS

1. In vitro determination of the affinity to the $\beta_1$- and $\beta_2$-receptor subtype by competitive experiments For this purpose, mixtures with bovine heart membranes (90% of $\beta_1$, 10% of $\beta_2$) or rat lung membranes (25% of $\beta_1$, 75% of $\beta_2$) in tris-HCl (50 mM)/0.1% ascorbic acid (pH 7.4) were prepared with increasing concentrations of test substance and a fixed concentration (1 nM) of the radioligand $^3$H-dihydroalprenolol. The unspecific binding was determined with $10^{-4}$ M isoproterenol.

After incubation for 60 minutes at 25° C., the mixtures were diluted with buffer and immediately filtered over glass filters (GF/F, Whatman), and the amount of the radioligand retained on the filter was determined by means of liquid scintillation measurement. Two experiments were carried out with three batches.

The competition constants (Ki values in nM) were calculated by nonlinear regression analysis on an IBM computer using the program ligand due to Munson and Rodbard (Anal. Biochem. 107 (1980), 220).

TABLE 1

Inhibition of the specific $^3$H-dihydroalprenolol binding in bovine heart membranes (90% of $\beta_1$) and rat lung membranes (25% of $\beta_1$, 75% of $\beta_2$)
Competition constants (K$_i$) with confidence limits (CL), determined by simultaneous fitting of the competition curves

| Substance | Heart K$_i$ (nM) | Lung K$_i$ (nM) |
|---|---|---|
| (R,S)-propafenone | 74 (70-77) | 32 (31-34) |
| (R)-propafenone | 788 (708-868) | 257 (237-276) |
| (S)-propafenone | 59 (53-64) | 14 (13-15) |

2. Determination of the antiarrhythmic action in aconitine-induced arrhythmia of the rat
The experimental animals used were male Sprague-Dawley rats weighing from 180 to 300 g. Anaesthesia was effected intraperitoneally with 100 mg/kg of thiobuta-

TABLE 1-continued

Inhibition of the specific $^3$H-dihydroalprenolol binding in bovine heart membranes (90% of $\beta_1$) and rat lung membranes (25% of $\beta_1$, 75% of $\beta_2$)
Competition constants (K$_i$) with confidence limits (CL), determined by simultaneous fitting of the competition curves

| Substance | Heart K$_i$ (nM) | Lung K$_i$ (nM) |
|---|---|---| barbital. To induce arrhythmias, aconitine was infused at a rate of 5 μg per kg per minute. The test substances were administered intravenously 2 minutes before the beginning of the aconitine infusion. The parameter measured was the duration of the aconitine infusion when the first arrhythmias (loss of P, ventricular extrasystoles and tachycardias) appeared in the ECG of the animals. In untreated animals, the aconitine-induced arrhythmia occurred after 3.3 ± 0.11 minutes (n = 120). The ED 50% was determined from the linear relationship between log dose (mg/kg) of the test substances and the relative prolongation of aconitine infusion duration (Δ%).

2. Determination of the antiarrhythmic action in aconitine-induced arrhythmia of the rat The experimental animals used were male Sprague-Dawley rats weighing from 180 to 300 g. Anaesthesia was effected intraperitoneally with 100 mg/kg of thiobutabarbital. To induce arrhythmias, aconitine was infused at a rate of 5 μg per kg per minute. The test substances were administered intravenously 2 minutes before the beginning of the aconitine infusion. The parameter measured was the duration of the aconitine infusion when the first arrhythmias (loss of P, ventricular extrasystoles and tachycardias) appeared in the ECG of the animals. In untreated animals, the aconitine-induced arrhythmia occurred after 3.3±0.11 minutes (n=120). The ED 50% was determined from the linear relationship between log dose (mg/kg) of the test substances and the relative prolongation of aconitine infusion duration (Δ%).

TABLE 2

Antiarrhythmic effect of (R,S)-propafenone and its enantiomers on aconitine-induced arrhythmias in anaesthetized rats 5 minutes after intravenous administration; ED 50%; 95% confidence limit

| Substance | Antiarrhythmic effect on aconitine-induced arrhythmias ED 50% mg/kg |
|---|---|
| (R,S)-propafenone | 0.724 (0.56-0.935) |
| (R)-propafenone | 0.801 (0.44-1.46) |
| (S)-propafenone | 0.676 (0.412-1.11) |

The Examples which follow illustrate the invention

EXAMPLE 1

(R)-propafenone . HCl 19 ml (0.12 mole) of diethyl azodicarboxylic acid were added dropwise at 0°-5° C. to a solution of 22.6 g (0.1 mole) of 2'-hydroxy-3-phenylpropiophenone (I), 8.9 g (0.12 mole) of (S)-glycidol and 31.6 g (0.12 mole) of triphenylphosphine. The mixture was stirred overnight at room temperature and the solvent was distilled off. The oily residue was refluxed with 100 ml of propylamine for 8 hours, after which the excess propylamine was distilled off. 50 ml of 5 N HCl were added, and the mixture was then heated for 1 hour at 50° C. and filtered. Crystals were precipitated on cooling, and were filtered off under suction, washed with ethanol and dried. 19.7 g (52%) of (R)-propafenone . HCl, mp. 177°–178° C., $[\alpha]_D^{23} = +6.4°$ (C=1, CH$_3$OH), were obtained.

EXAMPLE 2

(S)-propafenone . HCl 0.8 g of 2'-hydroxy-3-phenylpropiophenone was added at 0° C. to a suspension of 3.7 millimoles of NaH in 10 ml of tetrahydrofuran. A clear solution was formed. 0.7 g (3.3 millimoles) of glycidyl (S)-trifluoromethanesulfonate was added dropwise at −30° C., and the solution was left to stand at −20° C. The mixture was poured onto ice and extracted with CH$_2$Cl$_2$. The organic phase was dried and the solvent was distilled off. The oily residue was stirred overnight in 5 ml of n-propylamine. Excess amine was distilled off, the residue was dissolved in 5 ml of ethanol and HCl in ether was added. Colorless crystals formed and were filtered off under suction and dried. 0.6 g of (S)-propafenone . HCl, mp. 178°–179° C., $[\alpha]_D^{23} = -6.3°$ (C=1, CH$_3$OH), was obtained.

We claim:

1. A method for the treatment of arrhythmias in an older patient or a patient suffering from hypotension and cardiac insufficiency, for whom β-blockers are contraindicated, by administering to said patient an effective amount of (R)-propafenone alone.

2. The method of claim 1, wherein arrhythmias in an older patient is treated.

3. The method of claim 1, wherein a patient suffering from hypotension and cardiac insufficiency is treated.

4. The method of claim 2, comprising administering to said patient from 14 to 1400 mg of said (R)-propafenone alone.

5. The method of claim 2, comprising administering to said patient from 14 to 1400 mg of said (R)-propafenone per single dose.

6. The method of claim 2, comprising administering to said patient from 14 to 1400 mg of said (R)-propafenone.

7. The method of claim 2, comprising administering to said patient from 14 to 1400 mg of said (R)-propafenone per single dose.

* * * * *